United States Patent
Patel et al.

(10) Patent No.: US 9,211,325 B2
(45) Date of Patent: Dec. 15, 2015

(54) PEPTIDE ADJUVANTS

(71) Applicants: Ami Patel, Winnipeg (CA); Darwyn Kobasa, Winnipeg (CA); Gary Kobinger, Winnipeg (CA); Shawn Babiuk, Winnipeg (CA)

(72) Inventors: Ami Patel, Winnipeg (CA); Darwyn Kobasa, Winnipeg (CA); Gary Kobinger, Winnipeg (CA); Shawn Babiuk, Winnipeg (CA)

(73) Assignee: Her Majesty the Queen in Right of Canada as Represented by the Minister of Health, Winnipeg, Manitoba (CA)

( * ) Notice: Subject to any disclaimer, the term of this patent is extended or adjusted under 35 U.S.C. 154(b) by 331 days.

(21) Appl. No.: 13/833,523

(22) Filed: Mar. 15, 2013

(65) Prior Publication Data

US 2013/0323285 A1 Dec. 5, 2013

Related U.S. Application Data

(62) Division of application No. 13/129,514, filed as application No. PCT/CA2009/001707 on Nov. 30, 2009, now Pat. No. 8,404,243.

(60) Provisional application No. 61/118,533, filed on Nov. 28, 2008.

(51) Int. Cl.
*A61K 39/395* (2006.01)
*A61K 39/39* (2006.01)
*C07K 7/06* (2006.01)
*A61K 39/00* (2006.01)

(52) U.S. Cl.
CPC . *A61K 39/39* (2013.01); *C07K 7/06* (2013.01); *A61K 2039/55516* (2013.01)

(58) Field of Classification Search
None
See application file for complete search history.

(56) References Cited

U.S. PATENT DOCUMENTS

2004/0214272 A1* 10/2004 La Rosa ............... C07H 21/04
435/69.1

* cited by examiner

*Primary Examiner* — Yunsoo Kim
(74) *Attorney, Agent, or Firm* — Michael R. Williams; Ade & Company Inc.

(57) ABSTRACT

Adjuvant compositions comprising specific 5mer polypeptides in combination with antigen delivery systems and/or immunostimulatory molecules, such as immunostimulatory nucleic acid sequences, for enhancing the immune response of a coadministered antigen, are described.

9 Claims, 11 Drawing Sheets

Figure 1:
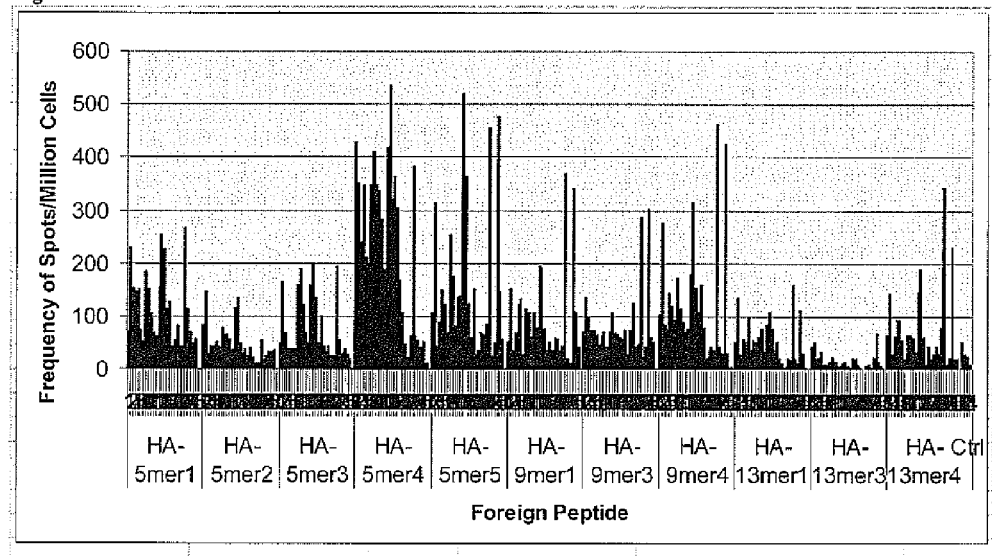

HK97 Survival: HA 100ug + 50ug Free 5mer4

- Control
- HA 100ug + 50ug Free 5mer4
- HA 100ug

A: Engerix-B (1ug) + free 5mer4 (50ug)
Purple = 2 weeks post immunization
Maroon = 4 weeks post immunization
Yellow = 6 weeks post-immunization
Blue = 8 weeks post immunization B: Engerix-B (1ug) alone
Purple =2 weeks post immunization
Maroon = 4 weeks post immunization
Yellow = 6 weeks post-immunization
Blue = 8 weeks post immunization A: Fluviral (5ug) + free 5mer4 (50ug)
Purple =2 weeks post immunization
Maroon = 4 weeks post immunization
Yellow = 6 weeks post-immunization
Blue = 8 weeks post immunization B: Fluviral (5ug) alone
Purple = 2 weeks post immunization
Maroon = 4 weeks post immunization
Yellow = 6 weeks post-immunization
Blue = 8 weeks post immunization

PEPTIDE ADJUVANTS

PRIOR APPLICATION INFORMATION

The instant application is a divisional application of U.S. Ser. No. 13/129,514, filed May 16, 2011, which was a 371 of PCT Application CA2009/001707, filed Nov. 30, 2009, now abandoned, which claims the benefit of U.S. Provisional Patent Application 61/118,533, filed Nov. 28, 2008.

FIELD OF THE INVENTION

The present invention relates generally to adjuvants, immunogenic compositions, and methods useful for polynucleotide-based vaccination. The present invention provides compositions and methods useful for enhancing immune response, especially the humoral immune response of vertebrates

BACKGROUND OF THE INVENTION

Vaccine compositions often include immunological adjuvants to enhance immune responses. For example, Complete Freund's adjuvant (CFA) is a powerful immunostimulatory agent that has been successfully used with many antigens on an experimental basis. CFA includes three components: a mineral oil, an emulsifying agent, and killed mycobacteria, such as *Mycobacterium tuberculosis*. Aqueous antigen solutions are mixed with these components to create a water-in-oil emulsion. Although effective as an adjuvant, CFA causes severe side-effects, including pain, abscess formation and fever, primarily due to the presence of the mycobacterial component. CFA, therefore, is not used in human and veterinary vaccines.

Immunologic adjuvants help increase immune responses induced by vaccines. Different mechanisms have been proposed to explain the enhanced antigen specific immune response generated by adjuvanted vaccine. First, adjuvant can promote a slow release of the antigen exposing it to the immune system for a longer period of time and consequently stimulating a stronger and possibly better defined immune response. Second, adjuvant can also help delivery and uptake of the antigenic complex to antigen presenting cells (APCs) such as macrophages and dendritic cells which in turn can migrate to lymphoid organs and initiate a concerted response in interaction with T and B cells. Third, immune cells including APCs can be directly activated by adjuvant and then initiate a faster and stronger immune response through the subsequent stimulation of T and B cells. Oil-in-water emulsion ingested by macrophage which then can migrate to draining lymph nodes, or TLRs stimulating molecules such as unmethylated CpG dinucleotide-containing DNA, are examples of adjuvant acting mainly according to these mechanisms. An interesting paradigm regarding immune reaction is that immune responses are generally more robust when stimulated by an antigen of rare occurrence than by an antigen frequently encountered in nature. The present study explores the possibility of using short peptidic sequences not present or observed only once in known proteomes as immunomodulators to enhance vaccine-induced immune responses and protection against lethal viral infections.

SUMMARY OF THE INVENTION

According to a first aspect of the invention, there is provided a method of stimulating an immune response to an antigen comprising co-administering to an individual in need of such treatment an effective amount of a composition comprising an antigen and a peptide comprising at least one amino acid sequence as set forth in table 1.

According to a second aspect of the invention, there is provided an immunostimulatory peptide sequence consisting of a peptide as set forth in table 1.

According to a further aspect of the invention, there is provided a composition comprising an effective amount of an adjuvant peptide comprising an amino acid sequence selected from the group consisting of: KWCEC (SEQ ID No. 4); KYMCW (SEQ ID No. 12); CYWWW (SEQ ID No. 14); EHWCM (SEQ ID No. 15); FCCWW (SEQ ID No. 16); TCCMW (SEQ ID No. 17); TCWWH (SEQ ID No. 18); TCYWW (SEQ ID No. 19); WMICM (SEQ ID No. 20) and YWHMW (SEQ ID No. 21) and an antigen of interest.

According to another aspect of the invention, there is provided a method of stimulating an immune response or enhancing an immune response to an antigen comprising administering to an individual in need of or desirous of such treatment an effective amount of an adjuvant peptide comprising an amino acid sequence selected from the group consisting of: KWCEC (SEQ ID No. 4); KYMCW (SEQ ID No. 12); CYWWW (SEQ ID No. 14); EHWCM (SEQ ID No. 15); FCCWW (SEQ ID No. 16); TCCMW (SEQ ID No. 17); TCWWH (SEQ ID No. 18); TCYWW (SEQ ID No. 19); WMICM (SEQ ID No. 20) and YWHMW (SEQ ID No. 21).

According to another aspect of the invention, there is provided the use of an adjuvant peptide comprising an amino acid sequence selected from the group consisting of: KWCEC (SEQ ID No. 4); KYMCW (SEQ ID No. 12); CYWWW (SEQ ID No. 14); EHWCM (SEQ ID No. 15); FCCWW (SEQ ID No. 16); TCCMW (SEQ ID No. 17); TCWWH (SEQ ID No. 18); TCYWW (SEQ ID No. 19); WMICM (SEQ ID No. 20) and YWHMW (SEQ ID No. 21) for stimulating an immune response or enhancing an immune response to an antigen in an individual in need of or desirous of such treatment According to a further aspect of the invention, there is provided a method of preparing a medicament for stimulating an immune response or enhancing an immune response to an antigen comprising mixing an effective amount of an adjuvant peptide comprising an amino acid sequence selected from the group consisting of: KWCEC (SEQ ID No. 4); KYMCW (SEQ ID No. 12); CYWWW (SEQ ID No. 14); EHWCM (SEQ ID No. 15); FCCWW (SEQ ID No. 16); TCCMW (SEQ ID No. 17); TCWWH (SEQ ID No. 18); TCYWW (SEQ ID No. 19); WMICM (SEQ ID No. 20) and YWHMW (SEQ ID No. 21) with a suitable excipient.

BRIEF DESCRIPTION OF THE DRAWINGS

FIG. 1: Enzyme-linked immunosorbent spot (ELISPOT) T cell response following immunization. BALB/c mice were vaccinated I.M. with 50 μg of pCAGα-HA DNA vaccine containing either: 5mer1 (CHKWD (SEQ ID No.1)), 5mer2 (WHKCE (SEQ ID No. 2)), 5mer3 (CKWRC (SEQ ID No. 3)), 5mer4 (KWCEC (SEQ ID No. 4)), 5mer5 (DCWMD (SEQ ID No. 5)), 9mer1 (CWKCWCMFE (SEQ ID No. 6)), 9mer3 (WNWCMHWDC (SEQ ID No. 7)), 9mer4 (WHWCMMCWD (SEQ ID No. 8)), 13mer1 (HEHWCMMWHCCMI (SEQ ID No. 9)), 13mer3 (HMMCHWMCWCDMH (SEQ ID No. 10)), or 13mer4 (CHMMCHWMWCCMD (SEQ ID No. 11)) foreign peptide fused to the carboxyl-terminal end of HA. pCAGα-HA (50 ug) represents the baseline T cell response. Overlapping peptides spanning the entire Hanoi 2005 HA protein were pooled (10 peptides/pool) and used to restimulate the splenocytes. Splenocytes were harvested 10 days following vaccination and re-stimulated using peptide pools derived from HA. The data represents the frequency of spots per one million splenocytes. 4 mice were analyzed per group. From the data it can be seen that not all the hydrophobic peptides produced an equal immune response.

Figure 2:
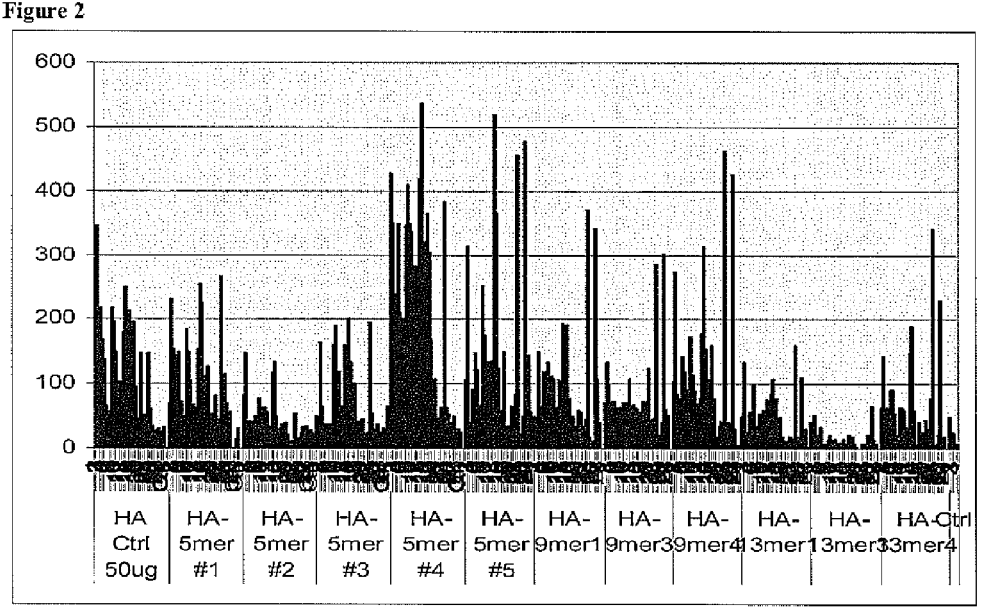
Figure 3:
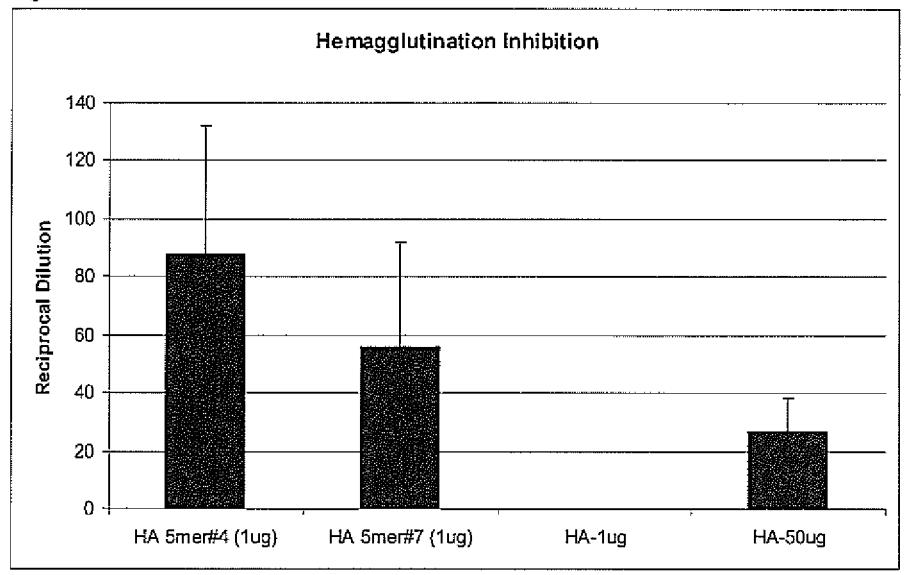
Figure 4:
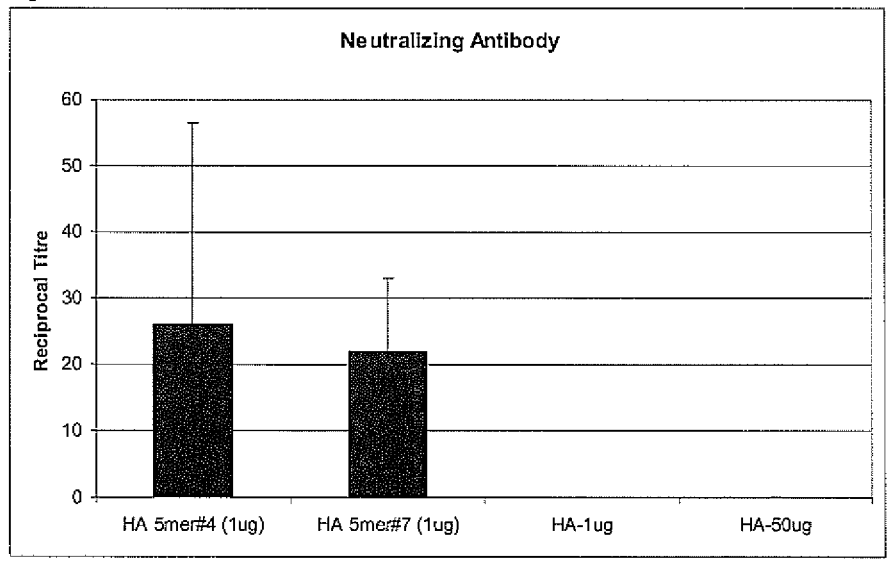
Figure 5:
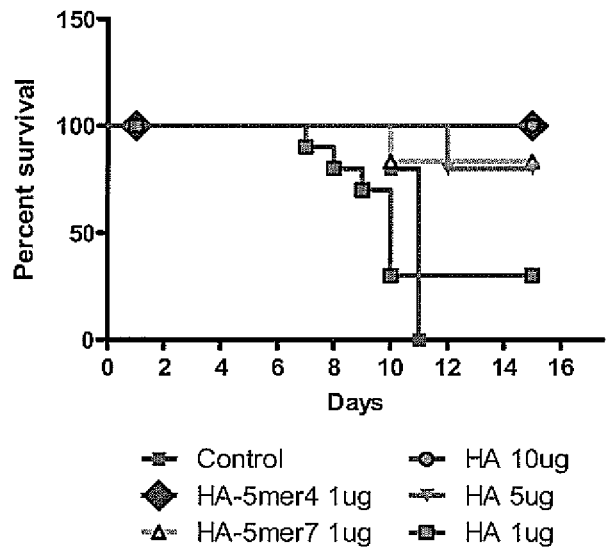
Figure 6:
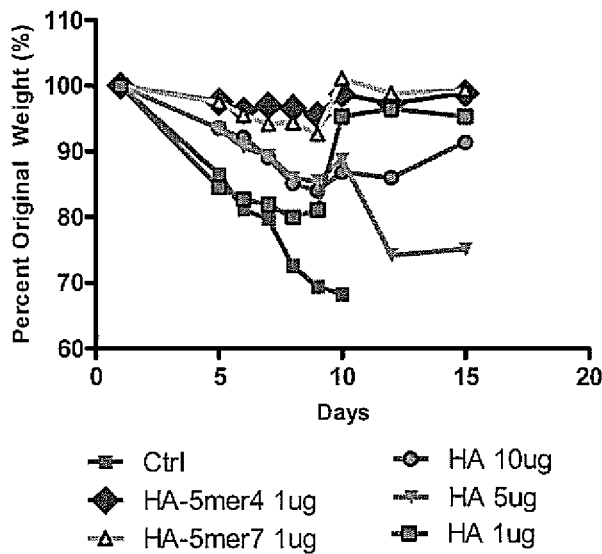
Figure 7:
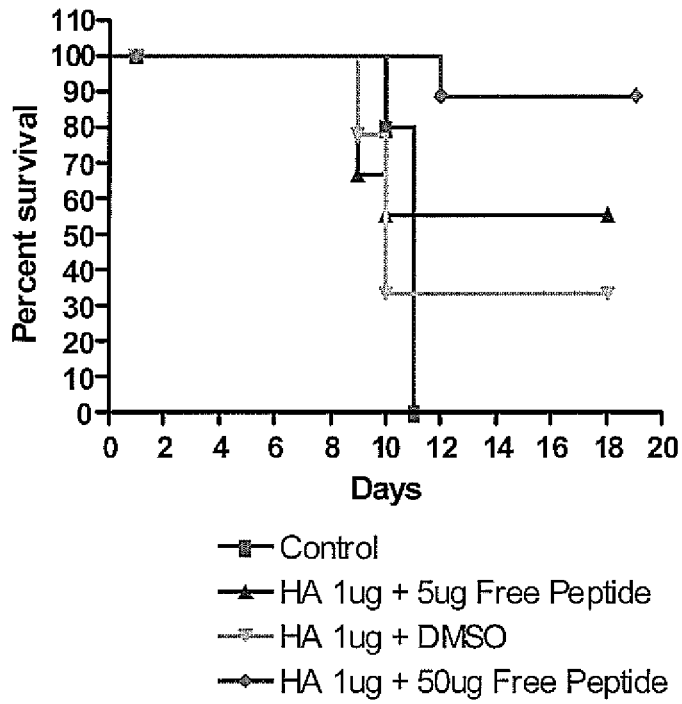
Figure 8:
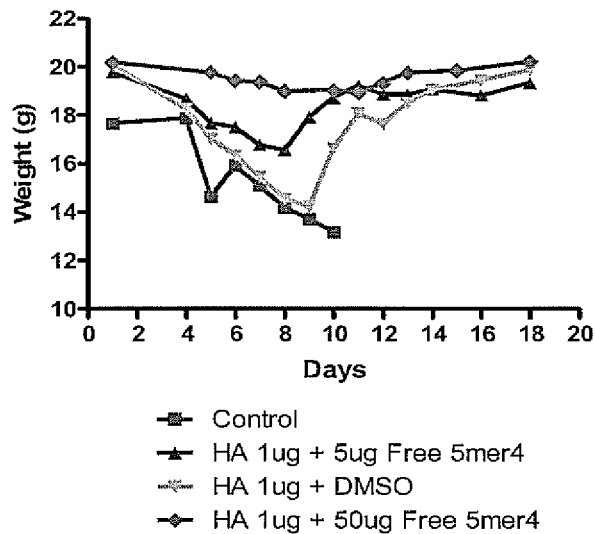
Figure 9:
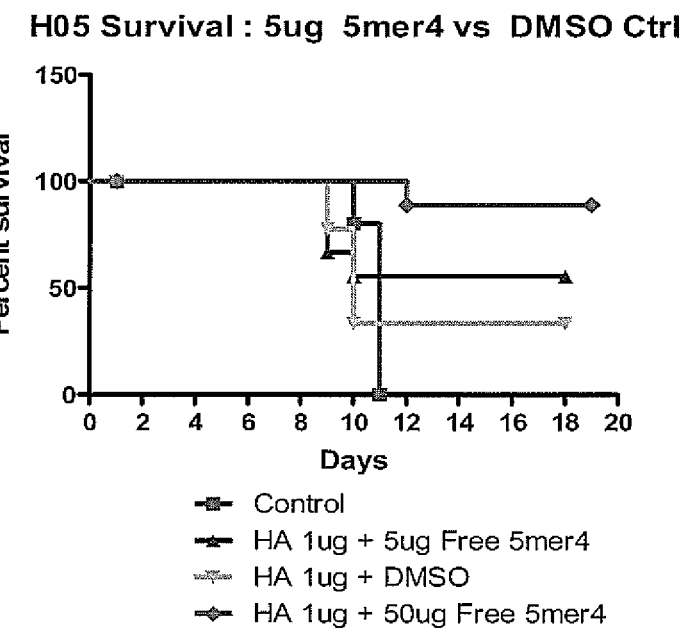
Figure 10:
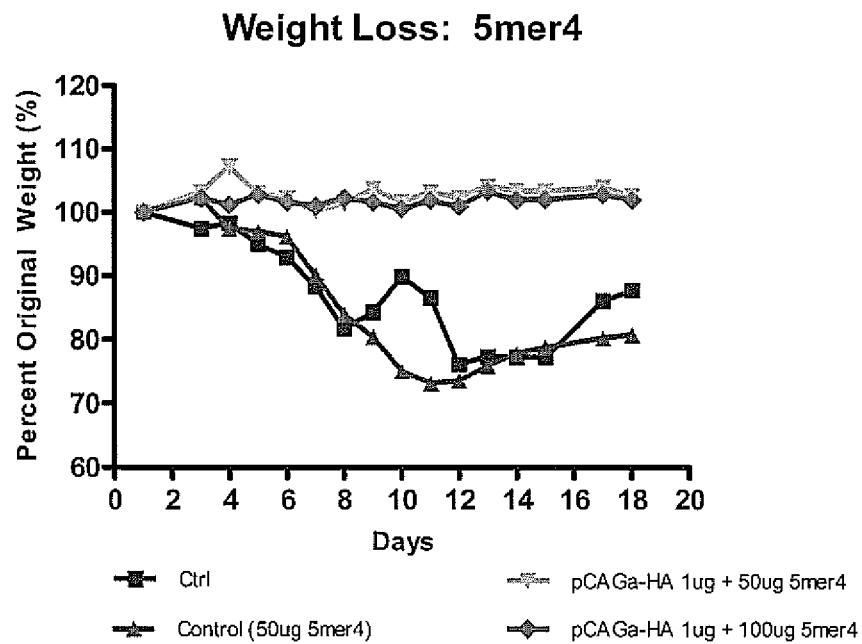
Figure 11:
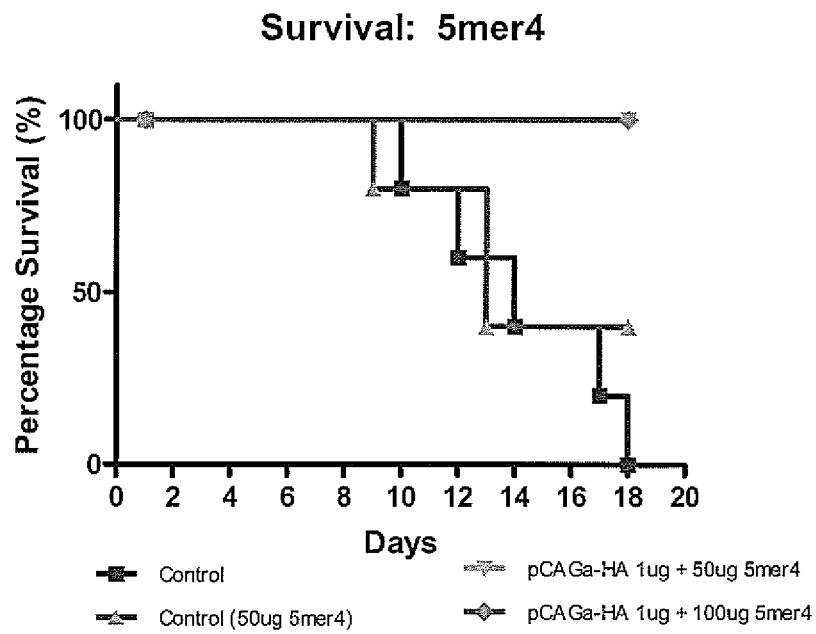
Figure 12:
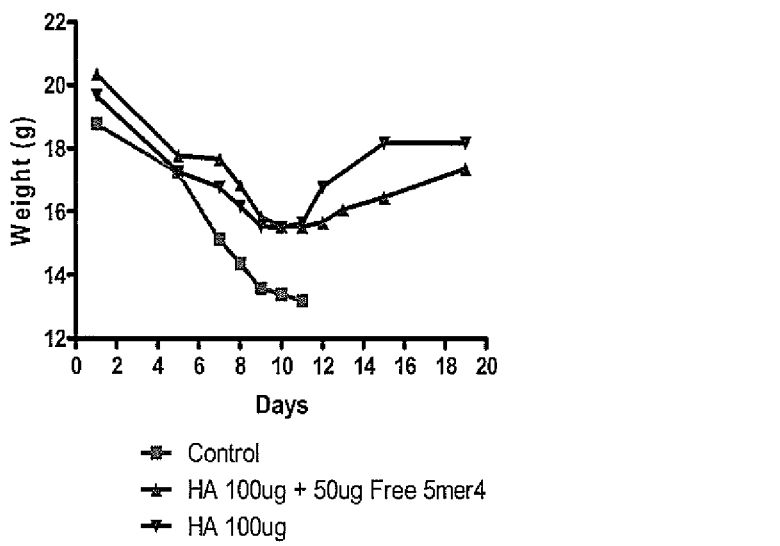
Figure 13:
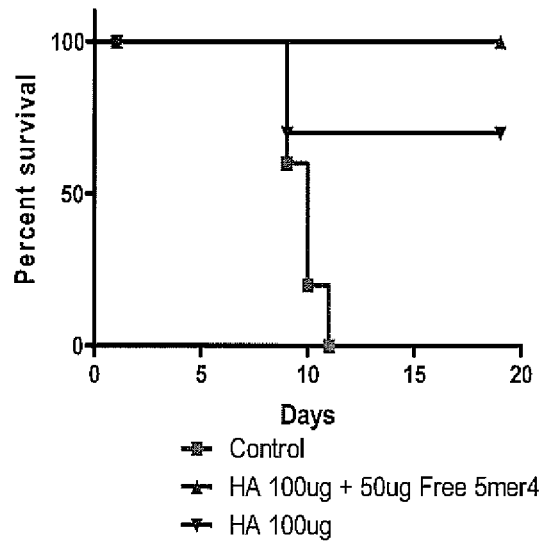
Figure 14A:
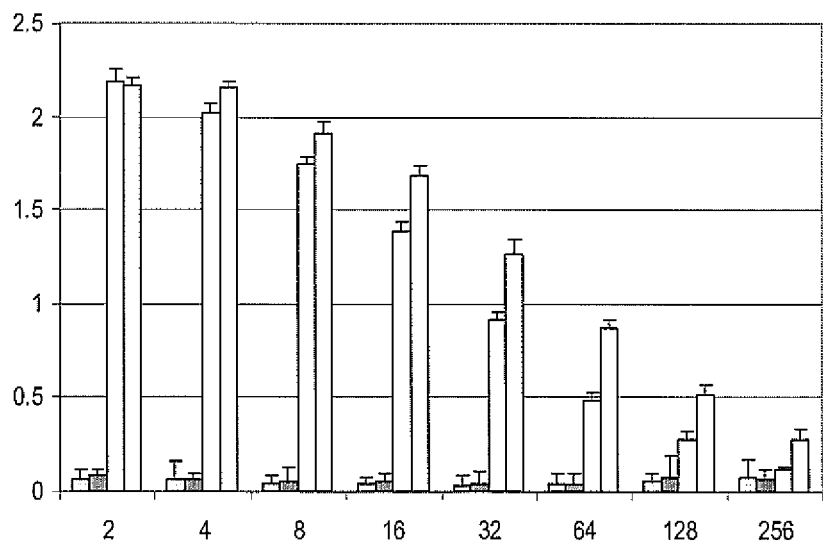
Figure 14B:
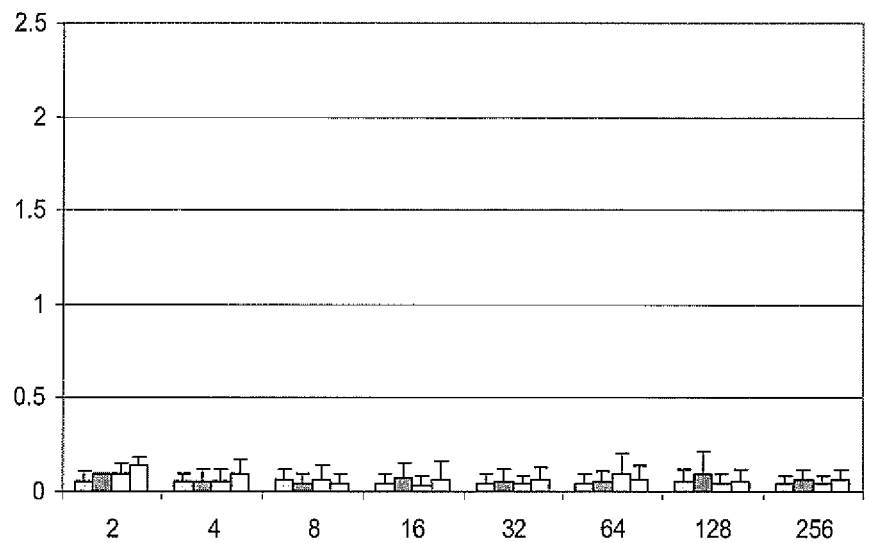
Figure 15A:
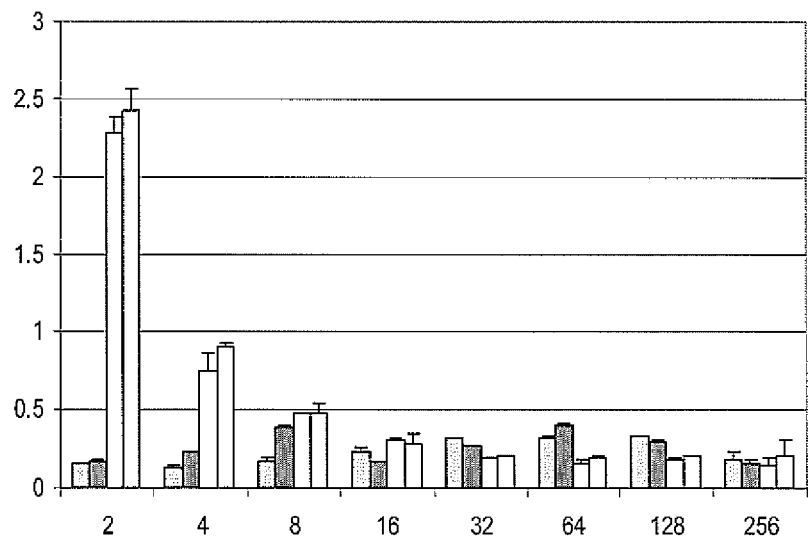
Figure 15B:
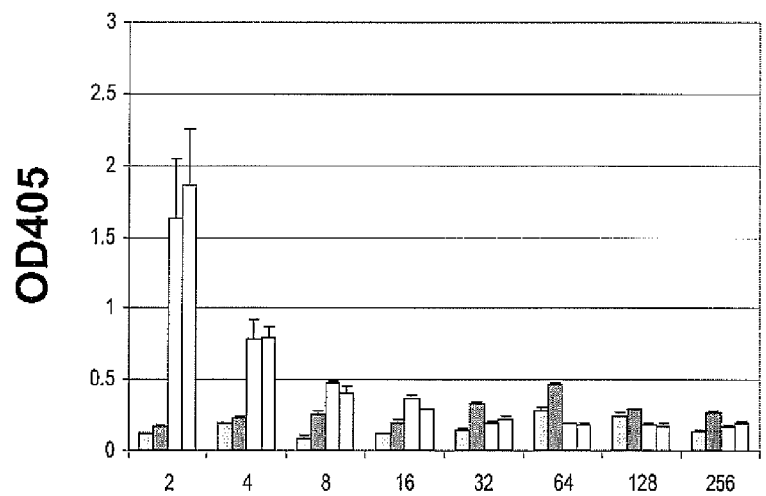
Figure 16:
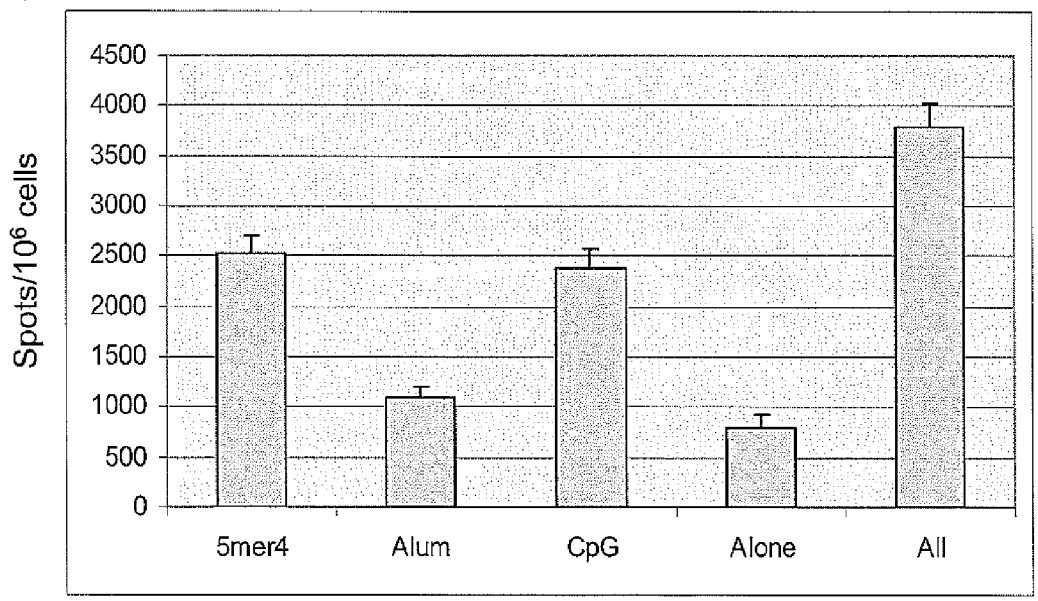

FIG. 2: Neutralizing antibody response following immunization was done to detect the presence of antibodies in sera that would be expected to counter the infection. BALB/c mice were vaccinated I.M. with 50 μg of pCAGα-HA DNA vaccine containing either: 5mer1 (SEQ ID No. 1), 5mer2 (SEQ ID No. 2), 5mer3 (SEQ ID No. 3), 5mer4 (SEQ ID No. 4), 5mer5 (SEQ ID No. 5), 9mer1 (SEQ ID No. 6), 9mer3 (SEQ ID No. 7), 9mer4 (SEQ ID No. 8), 13mer1 (SEQ ID No. 9), 13mer3 (SEQ ID No. 10), or 13mer4 (SEQ ID No. 11) foreign peptide and HA. Sera collected from immunized mice were evaluated by neutralization assays. For neutralization assays, sera were treated overnight at 37° C. with the receptor destroying enzyme (RDE) and then inactivated at 56° C. for 45 minutes. Two-fold serial dilutions of each sample, starting with a 1:10 dilution, were prepared in virus diluent and mixed with equal volume of the homologous influenza virus isolate used for immunization (100 plaque forming units [PFU] per well) and incubated at 37° C. for 60 minutes. The mixture was then transferred onto subconfluent MDCK cells in 96-well flat-bottomed plates and incubated for 5-10 minutes at room temperature. Control wells were infected with equal amount of viral vector without addition of serum or with non-immune control serum. 100 μl of virus diluent supplemented with 2.0 μg/ml TPCK-trypsin was then added to each well and plates were incubated at 37° C., 5% $CO_2$ for 48 hr. Cells were subsequently scored for the presence or the absence of cytopathic effects (CPE) under a light microscope. The highest serum dilution not exhibiting CPE was scored positive for neutralizing antibody and neutralization titers were reported as the reciprocal of this dilution. The peptides that generated a high T-cell response also generated a high neutralizing antibody response.

FIG. 3: Immune cell response and protective efficacy following immunization with foreign peptide recombinant DNA vaccine. BALB/c mice were vaccinated I.M. with 50 μg per mouse with pCAGα-HA DNA vaccine containing either 5mer4 (KWCEC (SEQ ID No. 4)) or 5mer7 (KYMCW (SEQ ID No. 12)) foreign peptide fused to the carboxyl-terminal end of HA. 5mer4 (SEQ ID No. 4) was selected because of the high T-cell and neutralizing antibody response. 5mer7 (SEQ ID No. 12) was selected due to the sequence similarity to 5mer4. Hemagglutination Inhibition. Serum was collected on day 25 post-vaccination. Serial dilutions were performed on sera obtained from vaccinated BALB/c mice and four agglutinating doses of virus were added to each well. The sera and virus were incubated with turkey red blood cells and hemagglutination inhibition (HI titer) was reported as the reciprocal of the highest dilution of serum which did not block the agglutination of erythrocytes. Control mice were vaccinated with phosphate buffered saline (PBS). Error bars represent the standard deviation of the data. From the data it was surprising to see that similar peptides behaved differently in the assay. Therefore the sequence of the peptide is important.

FIG. 4: Immune cell response and protective efficacy following immunization with foreign peptide recombinant DNA vaccine. BALB/c mice were vaccinated I.M. with 50 μg per mouse with pCAGα-HA DNA vaccine containing either 5mer4 (SEQ ID No. 4) or 5mer7 (SEQ ID No. 12) foreign peptide fused to the carboxyl-terminal end of HA. Neutralizing antibody (NAB) titers for pCAGα-HA-5mer4 or pCAGα-HA-5mer7 vaccinated mice. The experiment was repeated 3 times. Groups of 10 BALB/c mice were vaccinated I.M. with a single dose of either 1 μg pCAGα-HA-5mer4, 1 μg pCAGα-HA-5mer7, 1 μg pCAGα-HA, 5 μg pCAGα-HA or 10 μg pCAGα-HA per mouse. 28 days later they were challenged with 100 LD50 of H5N1 A\Hanoi\30408\2005. Control mice were vaccinated with phosphate buffered saline (PBS). Error bars represent the standard deviation of the data. This shows that in the response raised is one that is effective at generating antibodies that can effectively neutralize virus.

FIG. 5: Immune cell response and protective efficacy following immunization with foreign peptide recombinant DNA vaccine. BALB/c mice were vaccinated I.M. with 50 μg per mouse with pCAGα-HA DNA vaccine containing either 5mer4 (SEQ ID No. 4) or 5mer7 (SEQ ID No. 12) foreign peptide fused to the carboxyl-terminal end of HA. 28 days later they were challenged with 100 LD50 of H5N1 A\Hanoi\30408\2005 and percent survival over time measured. Control mice were vaccinated with phosphate buffered saline (PBS). Error bars represent the standard deviation of the data. This data demonstrates that vaccination using peptides as adjuvants provided a greater level of protection than antigen alone. There is also a dose response observed with the adjuvant and that the adjuvant can result in a stronger immune response with lower levels of antigen FIG. 6: Immune cell response and protective efficacy following immunization with foreign peptide recombinant DNA vaccine. BALB/c mice were vaccinated I.M. with 50 μg per mouse with pCAGα-HA DNA vaccine containing either 5mer4 (SEQ ID No. 4) or 5mer7 (SEQ ID No. 12) foreign peptide fused to the carboxyl-terminal end of HA. 28 days later they were challenged with 100 LD50 of H5N1 A\Hanoi\30408\2005 and weight measured. Control mice were vaccinated with phosphate buffered saline (PBS). Error bars represent the standard deviation of the data. This demonstrates that vaccination with the peptide-antigen combination protects the animals against weight loss which is a symptom of influenza infection.

FIG. 7: Protective efficacy following immunization with a free (exogenous) foreign peptide for homologous challenge. Groups of 10 BALB/c mice were vaccinated I.M. with a single dose of either 1 μg pCAGα-HA+5 μg 5mer4 (SEQ ID No. 4) as a free peptide, 1 μg pCAGα-HA+50 μg 5mer4 (SEQ ID No. 4) as a free peptide or 1 μg pCAGα-HA+Dimethyl sulfoxide (DMSO) per mouse. 28 days later they were challenged with 100 LD50 of H5N1 A/Hanoi/30408/2005. Data represents percent survival. Control mice were vaccinated with PBS. This data demonstrates that vaccination with the buffer alone does not induce protection against the influenza and that there is a dose effect with increasing amounts of peptide adjuvant.

FIG. 8: Protective efficacy following immunization with a free (exogenous) foreign peptide for homologous challenge. Groups of 10 BALB/c mice were vaccinated I.M. with a single dose of either 1 μg pCAGα-HA+5 μg 5mer4 (SEQ ID No. 4) as a free peptide, 1 μg pCAGα-HA+50 μg 5mer4 (SEQ ID No. 4) as a free peptide or 1 μg pCAGα-HA+Dimethyl sulfoxide (DMSO) per mouse. 28 days later they were challenged with 100 LD50 of H5N1 A/Hanoi/30408/2005. Data represents body weight over time. Control mice were vaccinated with PBS. This demonstrates that vaccination with the peptide plus antigen protects the animals against weight loss which is a symptom of influenza infection.

FIG. 9: Protective efficacy following immunization with a free (exogenous) foreign peptide for homologous challenge. Groups of 10 BALB/c mice were vaccinated I.M. with a single dose of either 1 μg pCAGα-HA+5 μg 5mer4 (SEQ ID No. 4) as a free peptide, 1 μg pCAGα-HA+50 μg 5mer4 (SEQ ID No. 4) as a free peptide or 1 µg pCAGα-HA+Dimethyl sulfoxide (DMSO) per mouse. 28 days later they were challenged with 100 LD50 of H5N1 A/Hanoi/30408/2005. Data represents percent survival. Control mice were vaccinated with PBS. This data demonstrates that vaccination with the buffer alone does not induce protection against the influenza and that there is a dose effect with increasing amounts of peptide adjuvant.

FIG. 10: Protective efficacy following immunization with different doses of free peptide 5mer4 (SEQ ID No. 4). Groups of 10 BALB/c mice were vaccinated I.M. with a single dose of 100 μg pCAGα-HA+ either 50 μg 5mer4 (SEQ ID No. 4) or 100 μg 5mer4 (SEQ ID No. 4) as a free peptide per mouse. 28 days later they were challenged with 100 LD50 of homologous Hanoi 2005 virus. Data represents body weight over time. Control mice were vaccinated with PBS or 50 μg of the free peptide. This demonstrates that vaccination with the peptide plus Antigen protects the animals against weight loss which is a symptom of influenza infection.

FIG. 11: Protective efficacy following immunization with different doses of free peptide 5mer4. Groups of 10 BALB/c mice were vaccinated I.M. with a single dose of 100 μg pCAGα-HA+ either 50 μg 5mer4 (SEQ ID No. 4) or 100 μg 5mer4 (SEQ ID No. 4) as a free peptide per mouse. 28 days later they were challenged with 100 LD50 of homologous Hanoi 2005 virus. Data represents percent survival. Control mice were vaccinated with PBS or 50 ug of the free peptide. This demonstrates that the effect requires both antigen and adjuvant to be effective in raising a specific immune response.

FIG. 12: Protective efficacy following immunization with a free foreign peptide for heterologous challenge. Groups of 10 BALB/c mice were vaccinated I.M. with a single dose of 100 μg pCAGα-HA+50 μg 5mer4 (SEQ ID No. 4) as a free peptide per mouse. 28 days later they were challenged with 100 LD50 of mouse-adapted H5N1 A\Hong Kong\483\1997. Data represents percent body weight loss over time. Control mice were vaccinated with PBS. This demonstrates that vaccination with the peptide plus antigen protects the animals against weight loss which is a symptom of influenza infection.

FIG. 13: Protective efficacy following immunization with a free foreign peptide for heterologous challenge. Groups of 10 BALB/c mice were vaccinated I.M. with a single dose of 100 μg pCAGα-HA+50 μg 5mer4 (SEQ ID No. 4) as a free peptide per mouse. 28 days later they were challenged with 100 LD50 of mouse-adapted H5N1 A\Hong Kong\483\1997. Data represents percent survival. Control mice were vaccinated with PBS. This demonstrates the efficacy of the vaccination procedure against heterologous viruses.

FIG. 14: Enzyme-linked immunosorbent assay (ELISA) following vaccination with the Hepatitis B vaccine (Engerix-B). BALB/c mice were vaccinated I.M. with the equivalent of 1 ug of the Engerix-B vaccine with (A) 50 ug of free peptide or (B) without peptide as a control. Serum was obtained from the mice at weeks 2, 4, 6, and 8 following vaccination. Total anti-FIBS antibodies were detected using a commerical ELISA kit. This data indicates a much stronger immune response is generated in the presence of antigen plus peptide than with antigen alone. The time course of immune response is as expected.

FIG. 15: Enzyme-linked immunosorbent assay (ELISA) following vaccination with the seasonal influenza (Fluviral 2008-2009) vaccine. BALB/c mice were vaccinated I.M. with the equivalent of 5 ug of the Fluviral vaccine with (A) 50 ug of free peptide or (B) without peptide as a control. Serum was obtained from the mice at weeks 2, 4, 6, and 8 following vaccination. Total anti-influenza IgG antibodies were detected using a commercial ELISA kit. This data demonstrates that even in the presence of high levels of antigen, the peptide will boost immune response.

FIG. 16: Enzyme-linked immunosorbent spot (ELISPOT) T cell response following immunization. BALB/c mice were vaccinated I.M. with 50 μg of pCAGα-HA DNA vaccine+50 ug of 5mer4 (SEQ ID No. 4), CpG-ODN (10 μg), alum (Alhydrogel, 450 ug), a combination of all three, or HA alone. Splenocytes were harvested 10 days following vaccination and re-stimulated using peptide pools derived from HA. The data represents the frequency of spots per one million splenocytes. 4 mice were analyzed per group. This data shows that the immune response generated when using the peptide is stronger than that generated with alum alone and comparable to that generated by CpG. Also, there is an apparent additive effect when the adjuvants are combined.

FIG. 17: Enzyme-linked immunosorbent spot (ELISPOT) T cell response following immunization. BALB/c mice were vaccinated I.M. with 50 μg of pCAGα-HA DNA vaccine alone or combined with pools of 10 5mer peptides. Splenocytes were harvested 10 days following vaccination and re-stimulated using peptide pools derived from HA. The data represents the frequency of spots per one million splenocytes. Bars represent the total of all pools. 4 mice were analyzed per group. This approach enabled rapid screening of closely related peptides.

FIG. 18: Enzyme-linked immunosorbent spot (ELISPOT) T cell response following immunization. BALB/c mice were vaccinated I.M. with 50 μg of pCAGα-HA DNA vaccine alone or combined with 50 ug of a 5mer from an immunodominant pool. Splenocytes were harvested 10 days following vaccination and re-stimulated using peptide pools derived from HA. The data represents the frequency of spots per one million splenocytes. Bars represent the total of all pools. 4 mice were analyzed per group. This data shows that despite single amino acid changes in peptide sequence, there can be a large difference in the strength of the T-cell response that is generated.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Adjuvant compositions comprising specific 5mer polypeptides in combination with antigen delivery systems and/or immunostimulatory molecules, such as immunostimulatory nucleic acid sequences, for enhancing the immune response of a coadministered antigen, are described. The present invention is based in part on the surprising discovery that the use selected hydrophobic peptides in combination with antigens provides for significantly higher antibody titers to a coadministered antigen, than those observed without such delivery systems or using traditional adjuvants. The use of such combinations provides a safe and effective approach for enhancing the immunogenicity of a variety of vaccine antigens for use in both prophylactic and therapeutic compositions.

The practice of the present invention will employ, unless otherwise indicated, conventional methods of chemistry, biochemistry, recombinant DNA techniques and immunology, within the skill of the art. Such techniques are explained fully in the literature. See, e.g., Fundamental Virology, 2nd Edition, vol. I & II (B. N. Fields and D. M. Knipe, eds.); Handbook of Experimental Immunology, Vols. I-IV (D. M. Weir and C. C. Blackwell eds., Blackwell Scientific Publications); T. E. Creighton, Proteins: Structures and Molecular Properties (W. H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.).

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

The following amino acid abbreviations are used throughout the text:

Alanine: Ala (A) Arginine: Arg (R) Asparagine: Asn (N) Aspartic acid: Asp (D) Cysteine: Cys (C) Glutamine: Gln (O) Glutamic acid: Glu (E) Glycine: Gly (G) Histidine: H is (H) Isoleucine: Ile (I) Leucine: Leu (L) Lysine: Lys (K) Methionine: Met (M) Phenylalanine: Phe (F) Proline: Pro (P) Serine: Ser (S) Threonine: Thr (T) Tryptophan: Trp (W) Tyrosine: Tyr (Y) Valine: Val (V)

DEFINITIONS

In describing the present invention, the following terms will be employed, and are intended to be defined as indicated below.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

By "antigen" is meant a molecule, which contains one or more epitopes that will stimulate a host's immune system to make a cellular antigen-specific immune response when the antigen is presented, or a humoral antibody response. The term "antigen" as used herein denotes both subunit antigens, i.e., proteins which are separate and discrete from a whole organism with which the antigen is associated in nature, as well as killed, attenuated or inactivated bacteria, viruses, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses a therapeutic or immunogenic protein, or antigenic determinant in vivo, such as in gene therapy and nucleic acid immunization applications, is also included in the definition of antigen herein. Further, for purposes of the present invention, antigens can be derived from any of several known viruses, bacteria, parasites and fungi, as well as any of the various tumor antigens.

An "immunological response" to a selected antigen or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host. The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., J. Immunol. (1993) 151:4189-4199; Doe et al., Eur. J. Immunol. (1994) 24:2369-2376.

The terms "effective amount" or "pharmaceutically effective amount" of an adjuvant composition and antigen, as provided herein, refer to a nontoxic but sufficient amount of the composition to provide the desired response, such as an immunological response, and optionally, a corresponding therapeutic effect, or in the case of delivery of a therapeutic protein, an amount sufficient to effect treatment of the subject, as defined below. As will be pointed out below, the exact amount required will vary from subject to subject, depending on the species, age, and general condition of the subject, the severity of the condition being treated, and the particular macromolecule of interest, mode of administration, and the like. An appropriate "effective" amount in any individual case may be determined by one of ordinary skill in the art using routine experimentation.

The "antigen delivery system" comprises the adjuvant composition, and antigen and other buffers and substances which may be used to stabilize or act as carriers for the combination.

In a first embodiment, the peptides are used in conjunction with antigens to generate a humoral and cellular response aimed to prevent an infectious disease by co-administering a peptide with an antigen.

In yet another embodiment, the subject invention is directed to a method of stimulating an immune response in a vertebrate subject which comprises administering to the subject an effective amount or a therapeutically effective amount of a selected antigen and an adjuvant composition comprising a peptide as described herein. As will be appreciated by one of skill in the art, the antigen and the adjuvant peptide may be administered by a variety of means and under a variety of conditions within the invention. For example, there may be provided an antigen delivery system and/or an immunostimulatory molecule, wherein the adjuvant composition is capable of increasing the immune response to the selected antigen. The antigen may be present in the adjuvant composition or may be administered in a separate composition. If the antigen is delivered separately, it may be delivered to the same or different site, and may be delivered prior to, subsequent to, or concurrent with the adjuvant composition.

It is important to note that as described herein, the administration of the adjuvant peptide to the individual in need of or desirous of a stimulated immune response for example to an antigen may be done by a variety of means, for example, by administering the adjuvant peptide and the antigen together, separately or even at different locations as discussed herein and as known in the art. The adjuvant peptide may be administered as a purified or isolated peptide or may be fused to the antigen either chemically or genetically (i.e. a transgenic peptide comprising both a peptide antigen and the adjuvant peptide) or it may be administered as a nucleic acid comprising the adjuvant peptide which is arranged to be expressed following administration so that the adjuvant peptide is still administered to the individual.

In a related embodiment, the subject invention is directed to a method of preventing infectious disease by co-administering a selected peptide and one or more DNA sequences that can express protein(s) from the infectious agent. These agents could include viruses such as Hepatitis C, HIV, hemoragghic fevers and the like or other antigens where a strong T-cell response is desired. As will be appreciated b one of skill in the art, suitable agents for co-administration include but are by no means limited to DNA, RNA or protein vaccines, viral extracts and deactived viruses or bacteria.

In one aspect of the invention, there is provided a composition comprising an effective amount of an adjuvant peptide comprising an amino acid sequence selected from the group consisting of: KWCEC (SEQ ID No. 4); KYMCW (SEQ ID No. 12); CYWWW (SEQ ID No. 14); EHWCM (SEQ ID No. 15); FCCWW (SEQ ID No. 16); TCCMW (SEQ ID No. 17); TCWWH (SEQ ID No. 18); TCYWW (SEQ ID No. 19); WMICM (SEQ ID No. 20) and YWHMW (SEQ ID No. 21) and an antigen of interest.

In another aspect of the invention, there is provided a method of stimulating an immune response or enhancing an immune response to an antigen comprising administering to an individual in need of or desirous of such treatment an effective amount of an adjuvant peptide comprising an amino acid sequence selected from the group consisting of: KWCEC (SEQ ID No. 4); KYMCW (SEQ ID No. 12); CYWWW (SEQ ID No. 14); EHWCM (SEQ ID No. 15); FCCWW (SEQ ID No. 16); TCCMW (SEQ ID No. 17); TCWWH (SEQ ID No. 18); TCYWW (SEQ ID No. 19); WMICM (SEQ ID No. 20) and YWHMW (SEQ ID No. 21). The individual in need of or desirous of such treatment may be an individual who is being immunized, as discussed herein.

In one preferred embodiment, the adjuvant peptide is selected from the group consisting of KWCEC (SEQ ID No. 4); KYMCW (SEQ ID No. 12); TCCMW (SEQ ID No. 17); TCWWH (SEQ ID No. 18); and TCYWW (SEQ ID No. 19).

In another preferred embodiment, the adjuvant peptide is selected from the group consisting of FCCWW (SEQ ID No. 16); TCCMW (SEQ ID No. 17); TCWWH (SEQ ID No. 18); TCYWW (SEQ ID No. 19); and WMICM (SEQ ID No. 20)

In another preferred embodiment, the adjuvant peptide is selected from the group consisting of KWCEC (SEQ ID No. 4) and KYMCW (SEQ ID No. 12).

In another preferred embodiment, the adjuvant peptide is KWCEC (SEQ ID No. 4).

In a preferred embodiment, the 'effective amount' or 'therapeutically effective amount' of the adjuvant peptide is between about 50 µg and about 5 mg per dose or per administration. In a more preferred embodiment, the dosage is between about 50 µg and about 500 µg. As will be appreciated by one of skill in the art, the effective amount may vary according to the age, weight and condition of the individual to which it is being administered.

As discussed herein, the adjuvant peptide of the invention may be administered as 'free' peptides (that is, may be isolated peptides consisting of an amino acid sequence selected from the group consisting of: KWCEC (SEQ ID No. 4); KYMCW (SEQ ID No. 12); CYWWW (SEQ ID No. 14); EHWCM (SEQ ID No. 15); FCCWW (SEQ ID No. 16); TCCMW (SEQ ID No. 17); TCWWH (SEQ ID No. 18); TCYWW (SEQ ID No. 19); WMICM (SEQ ID No. 20) and YWHMW (SEQ ID No. 21). Alternatively, the amino acid sequence may be attached to or embedded within an antigenic peptide or a carrier peptide using means known in the art. In other embodiments, such a construct may be encoded by a nucleic acid molecule which may be administered to the individual such that the adjuvant peptide is expressed following administration as discussed herein.

As will be appreciated by one of skill in the art, any suitable antigen may be used in combination with the adjuvant peptide of the invention. In a particularly preferred embodiment, the antigen is an antigen from an infectious disease, for example, a deactivated or attenuated virus or bacterium, a viral or bacterial extract or a bacterial or viral peptide.

In another aspect of the invention, there is provided the use of the above-described adjuvant peptides for inducing or stimulating or enhancing an immune response in an individual in need of such treatment. As discussed above, the adjuvant peptides may be administered together with the antigen or may be administered separately or may be administered at different sites.

In another aspect of the invention, there is provided a method of preparing a medicament or composition for stimulating an immune response in an individual comprising mixing an adjuvant peptide as described herein with a suitable excipient, for example, a suitable vaccine excipient, carrier or diluent. In other embodiments, the medicament or composition or vaccine may be prepared by mixing the adjuvant peptide as described above with the desired antigen.

As discussed herein, the adjuvant peptides may be administered to any vertebrate but preferably are administered to humans or animals for example in veterinary applications. Accordingly, in some aspects of the invention, the 'individual' is a non-human animal or a non-human vertebrate animal. Alternatively, the adjuvant peptides may be used for research purposes.

EXAMPLES

Below are examples of specific embodiments for carrying out the present invention. The examples are offered for illustrative purposes only, and are not intended to limit the scope of the present invention in any way.

Example 1

Identification of Peptides

Proteome databases were screened using a computer algorithm looking for short 5-mers peptides of amino acids sequences occurring maximum once. This analysis generated 417 never observed and 1288 unique sequences of 5-mers peptide found only once in all known proteomes. Nine and thirteen-mers sequences were computer generated from the previously 417 identified 5-mers sequences absent from known proteomes. Six 5-mers, three 9-mers and three 13-mers of various predicted hydrophobicity values were randomly selected for functional analysis. The effect of each short peptide on the immune response was first analyzed by evaluating the T-cell response against the hemagglutinin (HA) antigen of the Hanoi 2005 avian influenza virus expressed from a pCAG-based DNA vaccine in Balb/c mice. Each 5-, 9- and 13-mers sequence was cloned in frame at the C-terminus of the HA antigen in order to facilitate expression and minimize potential experimental deviation originating from independent peptidic preparations of variable purity. Groups of 4 mice were vaccinated intramuscularly (I.M.) with 50 µg per mouse of each plasmid DNA encoding for HA in frame with each short peptide sequence and the T-cell response was monitored from splenocytes 10 days later. The same plasmid DNA encoding HA without additional sequences (pCAG-HA) was included as a benchmark control. A library of overlapping peptides covering the entire HA protein was used for re-stimulating splenocytes and IFN-g production was evaluated by ELISPOT as a measure of the T-cell response. FIG. 1 shows that pCAG-HA-5-mers #4 (SEQ ID No. 4) and #6 (DMCKW, SEQ ID No. 13) increased the IFN-g production following stimulation with several individual peptides from the HA library when compared to other modified pCAG-HA-5, 9 or 13-mers or with the unmodified pCAG-HA control. From the data, it can be concluded that 5mers worked better than 9mers or 13mers at generating a T-cell response. From the data is does not appear that there are any patterns regarding hydrophobicity or sequence that led to an increased T-cell response which was quite surprising. The hydrophobicities of the various peptides are listed in Table 1.

Figures 1, 17:
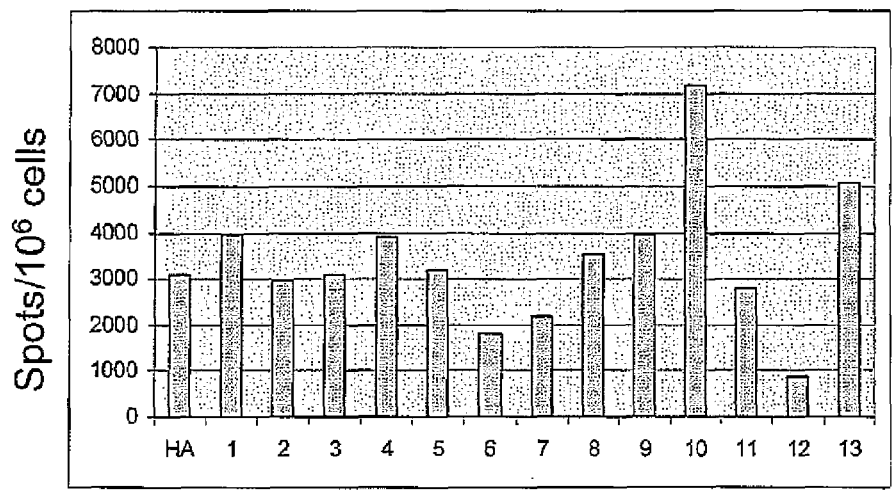
Figures 2, 17:
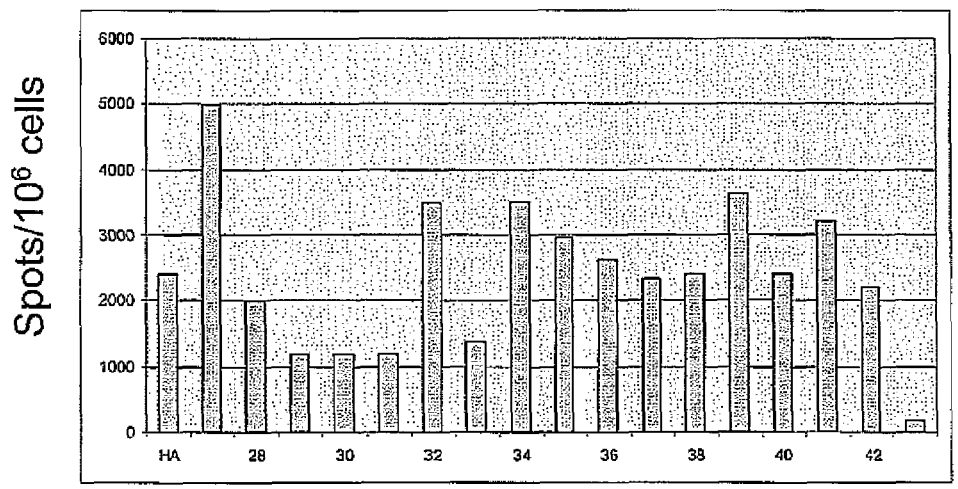
Figures 3, 17:
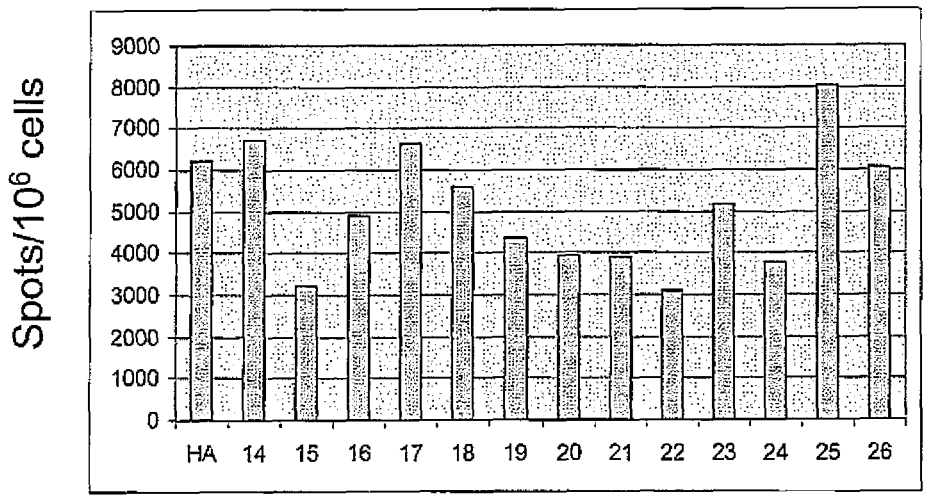
Figure 18:
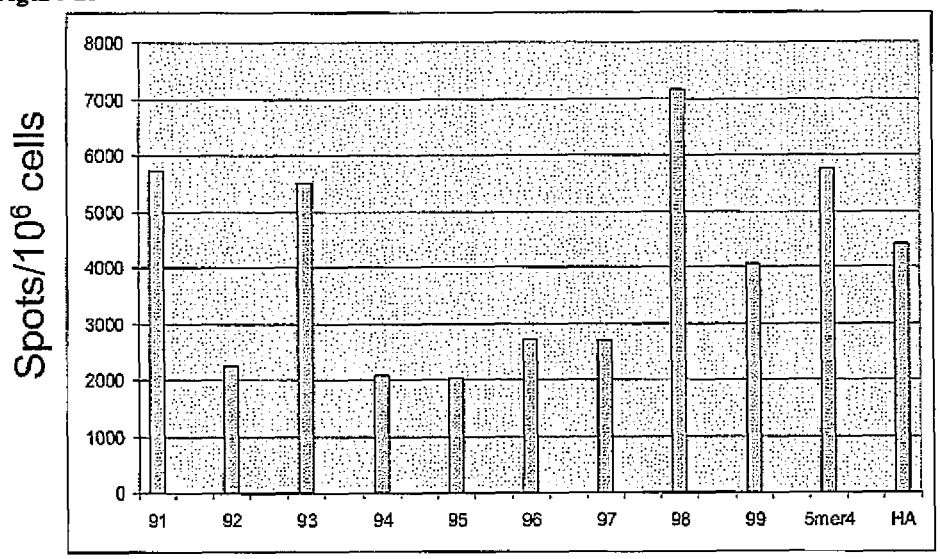

In addition neutralizing antibodies to the HA virus were measured and 5mer4 and 5mer7 were identified as peptides that caused a significant increase in neutralizing antibody response. Additional peptides were identified using a similar process. (see FIG. 17 and FIG. 18 It was surprising to find that very similar peptides could have a dramatically different effect on the observed response as shown in FIG. 18 (sequences shown in Table 2). Neutralizing antibodies are a marker for efficacy and it appears that vaccination with the 5mer4 (SEQ ID No. 4) and 5mer7 (SEQ ID No. 12) as adjuvants caused a significant antibody response while other 5mers (5mer1 (SEQ ID No. 1), 5mer2 (SEQ ID No. 2), 5mer3 (SEQ ID No. 3)) and the 9 and 13mers did not cause a strong neutralizing antibody response as shown in FIG. 2. Therefore to search for additional peptides that might also cause an increased immune response, groups of 10 randomly selected peptides were screened in the T-cell assay described above. For groups that demonstrated a T-cell response above baseline, individual peptides were screened in the assay. From the data it is surprising that closely related sequences had vastly different effects on the generation of a T-cell response. For example, peptide sequences CYWWW (91, SEQ ID No. 14) generated a significant T-cell response, but the peptide CYYWC (92, SEQ ID No. 22) which is different by only one amino acid generated a T-cell response that was below the baseline of HA alone. Similar differences were found for other peptides such the pair of EHWCM (93, SEQ ID No. 15)) and EMWCM (94, SEQ ID No. 23)) where the former generated a large T-cell response, but the latter did not. Peptides that generated a strong T-cell response in this assay are predicted to be good adjuvants based on the responses generated by 5mer4 (KWCEC, SEQ ID No. 4)) and 5mer7 (KYMCW (SEQ ID No. 12)) in expanded animal studies. It can also be observed from the data that the peptides that generated a high T-cell response also generated a high neutralizing antibody response which would be predicted to lead to an efficacious response in survival studies.

The anticipated dose of the peptide adjuvant in humans is expected to be between 50 µg and 5 mg, depending on the nature of the antigen. Most adjuvants are used at between 50 µg and 500 µg and this is expected to hold true for the selected peptides as well. To date, no serious toxicity has been observed with high doses of the selected peptides.

Example 2

Generation of a Protective Immune Response after Vaccination

Based on induced higher T-cell responses, pCAG-HA fused to either 5mer4 (SEQ ID No. 4) or 5mer7 (SEQ ID No. 12) were further studied in Balb/c mice. The antibody response was monitored by hemagglutination inhibition (HI) and neutralization (NAB) titration assays of sera 25 days after I.M. vaccination with each DNA vaccine including the unmodified HA as a control. The average HI reciprocal dilution titer was 85±40, 55±35 or 25±20 while the NAB titer was 25±30, 22±10 or undetectable for pCAG-HA-5-mer4, and 5mer7 or pCAG-HA respectively. To assess whether higher T and B-cell responses would correlate with enhanced protection, Balb/c mice were challenged with a lethal dose of Hanoi05 28 days after I.M. immunization with each HA-5mer4 and 5mer7. The DNA vaccine dose selected was based on the dose of 1 µg of unmodified pCAG-HA which was found to be the minimal dose tested to induce survival with 30%. Vaccination with 1 µg of pCAG-HA-5mer7 protected 80% of the animals from death with a weight loss of 5% while pCAG-HA-5-mers #4 induced 100% survival with no statistically significant weight loss and no clinical signs of disease. This demonstrates that using the peptide attached to the antigen as an adjuvant enables an effective immune response to be generated and provides protection from the effects typically found on influenza infection.

Example 3

Generation of a Protective Immune Response after Vaccination

Based on induced higher T-cell responses, pCAG-HA combined with 5 or 50 µg free peptides 5mer4 (SEQ ID No. 4) were further studied in Balb/c mice. The antibody response was monitored by hemagglutination inhibition (HI) and neutralization (NAB) titration assays of sera 25 days after I.M. vaccination with each DNA vaccine including the unmodified HA as a control. To assess whether higher T and B-cell responses would correlate with enhanced protection, Balb/c mice were challenged with a lethal dose of Hanoi05 28 days after I.M. immunization with each HA plus 5 or 50 µg of 5mer4 (SEQ ID No. 4). The DNA vaccine dose selected was based on the dose of 1 µg of unmodified pCAG-HA which was found to be the minimal dose tested to induce survival with 30%. Vaccination with 1 µg of pCAG-HA plus 5 ug 5mer4 (SEQ ID No. 4) protected 50% of the animals from death with minimal weight loss of while pCAG-HA plus 50 µg of 5mer4 induced 90% survival with no statistically significant weight loss and no clinical signs of disease. The unvaccinated control animals treated had 100% mortality. This demonstrates that using the free peptide as an adjuvant in conjunction with the antigen enables an effective immune response to be generated and provides protection from the effects typically found on influenza infection. This data also demonstrates that there is a dose response with different levels of adjuvant.

Example 4

Protective Efficacy Following Immunization with a Free Foreign Peptide for Heterologous Challenge Groups of 10 BALB/c mice were vaccinated I.M. with a single dose of 100 µg pCAGα-HA+ either 50 or 100 µg 5mer4 (SEQ ID No. 4) as a free peptide per mouse. Control mice were immunized with only 50 µg of 5mer4 or PBS. 28 days later they were challenged with 100 LD50 of mouse-adapted H5N1 A\Hong Kong\483\1997. the groups of mice that were immunized with pCAG α-HA+ either 50 or 100 µg 5mer4 (SEQ ID No. 4) both showed 100% survival while the control PBS group showed 100% mortality at 18 days post challenge. This demonstrates that using the free peptide as an adjuvant along with an antigen enables an effective immune response to be generated and provides protection from the effects typically found on influenza infection using related viruses which suggests that a strong, broad cross protective immune response has been generated.

Example 5

Adjuvant Works with Multiple Antigens

To demonstrate that the effect is not limited to influenza vaccines, BALB/c mice were vaccinated I.M. with the equivalent of 1 ug of the Hepatitis B vaccine (Engerix-B) Engerix-B vaccine with 50 μg of free peptide or without peptide as a control. Serum was obtained from the mice at weeks 2, 4, 6, and 8 following vaccination. Total anti-HBS antibodies were detected using a commercial ELISA kit. The response rate is quite dramatic, with the control Engerix B group showing a very small response at 8 weeks post immunization, and the Engerix B plus 50 μg of peptide showing a strong response at both 6 and 8 weeks post immunization. The generation of an antibody response at 6-8 weeks post immunization is typical of the type of response generated with vaccinations. This demonstrates that the free peptide functions with a wide range of antigen types.

Example 6

Adjuvant Works with Multiple Antigens

To demonstrate that the effect is not limited to influenza vaccines, BALB/c mice were vaccinated I.M. with the equivalent of 5 μg of the fluviral vaccine. Fluviral vaccine with (A) 50 ug of free peptide or (B) without peptide as a control. Serum was obtained from the mice at weeks 2, 4, 6, and 8 following vaccination. Total anti-HBS antibodies were detected using a commercial ELISA kit. The response rate is quite dramatic, with the control fluviral group showing a small response at 8 weeks post immunization, and the fluviral plus 50 μg of peptide showing a stronger response at both 6 and 8 weeks post immunization. Since this study was done with a relatively high level of antigen, it suggests that the amount of antigen required might be lower than typically expected to generate a strong immune response. This also demonstrates that the free peptide functions with a wide range of antigen types.

While the preferred embodiments of the invention have been described above, it will be recognized and understood that various modifications may be made therein, and the appended claims are intended to cover all such modifications which may fall within the spirit and scope of the invention.

TABLE 1

Selected sequences

| Amino Acid Sequence | Hydrophobicity | Molecular Weight | Name |
|---|---|---|---|
| KWCEC | 0.74* | 649.78 | 5mer4SEQ ID No. 4 |
| KYMCW | 1.00* | 711.90 | 5mer7SEQ ID No. 12 |
| CYWWW | 1.85 | 824.95 | SEQ ID No. 14 |
| EHWCM | 0.90 | 686.81 | SEQ ID No. 15 |
| FCCWW | 1.87* | 725.88 | SEQ ID No. 16 |
| TCCMW | 1.36* | 624.80 | SEQ ID No. 17 |
| TCWWH | 1.29* | 713.81 | SEQ ID No. 18 |
| TCYWW | 1.45* | 739.85 | SEQ ID No. 19 |
| WMICM | 1.80 | 682.92 | SEQ ID No. 20 |
| YWHMW | 1.36 | 803.94 | SEQ ID No. 21 |

Sequences of 5mers 91-99 (from FIG. 18)

| Sequence Number | Sequence |
|---|---|
| 91 (SEQ ID No. 14) | CYWWW |
| 92 (SEQ ID No. 22) | CYYWC |
| 93 (SEQ ID No. 15) | EHWCM |
| 94 (SEQ ID No. 23) | EMWCM |
| 95 (SEQ ID No. 24) | EWCMC |
| 96 (SEQ ID No. 25) | EWNCW |
| 97 (SEQ ID No. 26) | EYCWW |
| 98 (SEQ ID No. 16) | FCCWW |
| 99 (SEQ ID No. 27) | FHMMW |

The invention claimed is:

1. A composition comprising an effective amount of an adjuvant peptide comprising the amino acid sequence as set forth in SEQ ID NO:12 and an antigen of interest.

2. The composition according to claim 1 wherein the effective amount of the adjuvant peptide is between about 50 μg and about 5 mg.

3. The composition according to claim 1 wherein the effective amount of the adjuvant peptide is between about 50 μg and about 500 μg.

4. A method of stimulating an immune response or enhancing an immune response to an antigen of interest comprising administering to an individual in need of or desirous of such treatment an effective amount of an adjuvant peptide comprising the amino acid sequence as set forth in SEQ ID NO:12 and an antigen of interest.

5. The method according to claim 4 wherein the effective amount of the adjuvant peptide is between about 50 μg and about 5 mg.

6. The method according to claim 4 wherein the effective amount of the adjuvant peptide is between about 50 μg and about 500 μg.

7. A method of preparing a medicament for stimulating an immune response or enhancing an immune response to an antigen comprising mixing an effect amount of an adjuvant peptide comprising the amino acid sequence as set forth in SEQ ID NO:12 and an antigen of interest with a suitable excipient.

8. The method according to claim 7 wherein the effective amount of the adjuvant peptide is between about 50 μg and about 5 mg.

9. The method according to claim 7 wherein the effective amount of the adjuvant peptide is between about 50 μg and about 500 μg.

* * * * *

SEQUENCE LISTING

<160> NUMBER OF SEQ ID NOS: 27

<210> SEQ ID NO 1
<211> LENGTH: 5
<212> TYPE: PRT
<213> ORGANISM: artificial sequence
<220> FEATURE:
<223> OTHER INFORMATION: Short peptide sequence not known to occur in
      nature

<400> SEQUENCE: 1

Cys His Lys Trp Asp
1               5

<210> SEQ ID NO 2
<211> LENGTH: 5
<212> TYPE: PRT
<213> ORGANISM: artificial sequence
<220> FEATURE:
<223> OTHER INFORMATION: Short peptide sequence not known to occur in
      nature

<400> SEQUENCE: 2

Trp His Lys Cys Glu
1               5

<210> SEQ ID NO 3
<211> LENGTH: 5
<212> TYPE: PRT
<213> ORGANISM: artificial sequence
<220> FEATURE:
<223> OTHER INFORMATION: Short peptide sequence not known to occur in
      nature

<400> SEQUENCE: 3

Cys Lys Trp Arg Cys
1               5

<210> SEQ ID NO 4
<211> LENGTH: 5
<212> TYPE: PRT
<213> ORGANISM: artificial sequence
<220> FEATURE:
<223> OTHER INFORMATION: Short peptide sequence not known to occur in
      nature

<400> SEQUENCE: 4

Lys Trp Cys Glu Cys
1               5

<210> SEQ ID NO 5
<211> LENGTH: 5
<212> TYPE: PRT
<213> ORGANISM: artificial sequence
<220> FEATURE:
<223> OTHER INFORMATION: Short peptide sequence not known to occur in
      nature

<400> SEQUENCE: 5

Asp Cys Trp Met Asp
1               5

<210> SEQ ID NO 6
<211> LENGTH: 9
<212> TYPE: PRT
<213> ORGANISM: artificial sequence
<220> FEATURE:
<223> OTHER INFORMATION: Short peptide sequence not known to occur in

```
                              nature

<400> SEQUENCE: 6

Cys Trp Lys Cys Trp Cys Met Phe Glu
1               5

<210> SEQ ID NO 7
<211> LENGTH: 9
<212> TYPE: PRT
<213> ORGANISM: artificial sequence
<220> FEATURE:
<223> OTHER INFORMATION: Short peptide sequence not known to occur in
      nature

<400> SEQUENCE: 7

Trp Asn Trp Cys Met His Trp Asp Cys
1               5

<210> SEQ ID NO 8
<211> LENGTH: 9
<212> TYPE: PRT
<213> ORGANISM: artificial sequence
<220> FEATURE:
<223> OTHER INFORMATION: Short peptide sequence not known to occur in
      nature

<400> SEQUENCE: 8

Trp His Trp Cys Met Met Cys Trp Asp
1               5

<210> SEQ ID NO 9
<211> LENGTH: 13
<212> TYPE: PRT
<213> ORGANISM: artificial sequence
<220> FEATURE:
<223> OTHER INFORMATION: Short peptide sequence not known to occur in
      nature

<400> SEQUENCE: 9

His Glu His Trp Cys Met Met Trp His Cys Cys Met Ile
1               5                   10

<210> SEQ ID NO 10
<211> LENGTH: 13
<212> TYPE: PRT
<213> ORGANISM: artificial sequence
<220> FEATURE:
<223> OTHER INFORMATION: Short peptide sequence not known to occur in
      nature

<400> SEQUENCE: 10

His Met Met Cys His Trp Met Cys Trp Cys Asp Met His
1               5                   10

<210> SEQ ID NO 11
<211> LENGTH: 13
<212> TYPE: PRT
<213> ORGANISM: artificial sequence
<220> FEATURE:
<223> OTHER INFORMATION: Short peptide sequence not known to occur in
      nature

<400> SEQUENCE: 11

Cys His Met Met Cys His Trp Met Trp Cys Cys Met Asp
1               5                   10

<210> SEQ ID NO 12
```

```
<211> LENGTH: 5
<212> TYPE: PRT
<213> ORGANISM: artificial sequence
<220> FEATURE:
<223> OTHER INFORMATION: Short peptide sequence not known to occur in
      nature

<400> SEQUENCE: 12

Lys Tyr Met Cys Trp
1               5

<210> SEQ ID NO 13
<211> LENGTH: 5
<212> TYPE: PRT
<213> ORGANISM: artificial sequence
<220> FEATURE:
<223> OTHER INFORMATION: Short peptide sequence not known to occur in
      nature

<400> SEQUENCE: 13

Asp Met Cys Lys Trp
1               5

<210> SEQ ID NO 14
<211> LENGTH: 5
<212> TYPE: PRT
<213> ORGANISM: artificial sequence
<220> FEATURE:
<223> OTHER INFORMATION: Short peptide sequence not known to occur in
      nature

<400> SEQUENCE: 14

Cys Tyr Trp Trp Trp
1               5

<210> SEQ ID NO 15
<211> LENGTH: 5
<212> TYPE: PRT
<213> ORGANISM: artificial sequence
<220> FEATURE:
<223> OTHER INFORMATION: Short peptide sequence not known to occur in
      nature

<400> SEQUENCE: 15

Glu His Trp Cys Met
1               5

<210> SEQ ID NO 16
<211> LENGTH: 5
<212> TYPE: PRT
<213> ORGANISM: artificial sequence
<220> FEATURE:
<223> OTHER INFORMATION: Short peptide sequence not known to occur in
      nature

<400> SEQUENCE: 16

Phe Cys Cys Trp Trp
1               5

<210> SEQ ID NO 17
<211> LENGTH: 5
<212> TYPE: PRT
<213> ORGANISM: artificial sequence
<220> FEATURE:
<223> OTHER INFORMATION: Short peptide sequence not known to occur in
      nature

<400> SEQUENCE: 17
```

```
Thr Cys Cys Met Trp
1               5

<210> SEQ ID NO 18
<211> LENGTH: 5
<212> TYPE: PRT
<213> ORGANISM: artificial sequence
<220> FEATURE:
<223> OTHER INFORMATION: Short peptide sequence not known to occur in
      nature

<400> SEQUENCE: 18

Thr Cys Trp Trp His
1               5

<210> SEQ ID NO 19
<211> LENGTH: 5
<212> TYPE: PRT
<213> ORGANISM: artificial sequence
<220> FEATURE:
<223> OTHER INFORMATION: Short peptide sequence not known to occur in
      nature

<400> SEQUENCE: 19

Thr Cys Tyr Trp Trp
1               5

<210> SEQ ID NO 20
<211> LENGTH: 5
<212> TYPE: PRT
<213> ORGANISM: artificial sequence
<220> FEATURE:
<223> OTHER INFORMATION: Short peptide sequence not known to occur in
      nature

<400> SEQUENCE: 20

Trp Met Ile Cys Met
1               5

<210> SEQ ID NO 21
<211> LENGTH: 5
<212> TYPE: PRT
<213> ORGANISM: artificial sequence
<220> FEATURE:
<223> OTHER INFORMATION: Short peptide sequence not known to occur in
      nature

<400> SEQUENCE: 21

Tyr Trp His Met Trp
1               5

<210> SEQ ID NO 22
<211> LENGTH: 5
<212> TYPE: PRT
<213> ORGANISM: artificial sequence
<220> FEATURE:
<223> OTHER INFORMATION: Short peptide sequence not known to occur in
      nature

<400> SEQUENCE: 22

Cys Tyr Tyr Trp Cys
1               5

<210> SEQ ID NO 23
<211> LENGTH: 5
<212> TYPE: PRT
<213> ORGANISM: artificial sequence
<220> FEATURE:
```

```
<223> OTHER INFORMATION: Short peptide sequence not known to occur in
      nature

<400> SEQUENCE: 23

Glu Met Trp Cys Met
1               5

<210> SEQ ID NO 24
<211> LENGTH: 5
<212> TYPE: PRT
<213> ORGANISM: artificial sequence
<220> FEATURE:
<223> OTHER INFORMATION: Short peptide sequence not known to occur in
      nature

<400> SEQUENCE: 24

Glu Trp Cys Met Cys
1               5

<210> SEQ ID NO 25
<211> LENGTH: 5
<212> TYPE: PRT
<213> ORGANISM: artificial sequence
<220> FEATURE:
<223> OTHER INFORMATION: Short peptide sequence not known to occur in
      nature

<400> SEQUENCE: 25

Glu Trp Asn Cys Trp
1               5

<210> SEQ ID NO 26
<211> LENGTH: 5
<212> TYPE: PRT
<213> ORGANISM: artificial sequence
<220> FEATURE:
<223> OTHER INFORMATION: Short peptide sequence not known to occur in
      nature

<400> SEQUENCE: 26

Glu Tyr Cys Trp Trp
1               5

<210> SEQ ID NO 27
<211> LENGTH: 5
<212> TYPE: PRT
<213> ORGANISM: artificial sequence
<220> FEATURE:
<223> OTHER INFORMATION: Short peptide sequence not known to occur in
      nature

<400> SEQUENCE: 27

Phe His Met Met Trp
1               5
```